United States Patent [19]

Ryan

[11] Patent Number: 5,292,308
[45] Date of Patent: Mar. 8, 1994

[54] THREE PIECE INTRAVENOUS LINE CONNECTOR

[76] Inventor: Dana W. Ryan, 11520 SW. 22nd Ct., Davie, Fla. 33325

[21] Appl. No.: 57,525

[22] Filed: May 4, 1993

[51] Int. Cl.⁵ ............................................. A61M 25/00
[52] U.S. Cl. .................................... 604/86; 604/283; 604/905
[58] Field of Search .................. 604/86, 88, 201, 206, 604/240, 243, 244, 283, 905

[56] References Cited

U.S. PATENT DOCUMENTS

| | | |
|---|---|---|
| 1,687,324 | 2/1925 | Cook . |
| 3,986,508 | 10/1976 | Barrington ........................... 604/905 |
| 4,338,933 | 7/1982 | Baynard et al. .................... 604/905 |
| 4,511,359 | 4/1985 | Vaillancourt ........................ 604/411 |
| 4,559,043 | 12/1985 | Whitehouse et al. ............... 604/283 |
| 4,752,292 | 6/1988 | Lopez et al. ........................ 604/244 |
| 4,810,241 | 3/1989 | Rogers ................................ 604/28 |
| 4,946,445 | 8/1990 | Lynn ................................... 604/192 |
| 4,950,260 | 8/1990 | Bonaldo .............................. 604/283 |
| 4,981,469 | 1/1991 | Whitehouse et al. ................ 604/86 |
| 5,199,947 | 4/1993 | Lopez et al. ......................... 604/56 |

FOREIGN PATENT DOCUMENTS

| | | | |
|---|---|---|---|
| 0157224 | 10/1985 | European Pat. Off. . | |
| 9116938 | 11/1991 | World Int. Prop. O. | ........... 604/283 |

*Primary Examiner*—John D. Yasko
*Assistant Examiner*—Anthony Gutowski
*Attorney, Agent, or Firm*—David P. Gordon

[57] ABSTRACT

IV safety line connectors include a single piece male connector and a two piece female connector. The male connector has a luer on one end, one or more inwardly extending bayonet recesses on a middle portion and a reduced diameter second end enclosing a resilient septum. The female connector has a luer on one end and a two part receiving cylinder on the other with inwardly extending knobs. The luer and the first part of the cylinder are separated by a wall through which a hollow needle extends The connectors are mated by sliding the second end of the male connector into the receiving cylinder of the female connector with the knobs of the female connector being guided by the recesses of the male connector. The connectors are locked into place by bringing them together, and then rotating them such that knobs move past restrictions in the recesses and lock into place. The parts of the female connector are joined together by sonic welding or solvent bonding which is enhanced by providing one with a reduced inner diameter end and the other with a reduced outer diameter end so that the parts join in a male/female relationship. The ends of the two parts are preferably faceted to prevent relative rotation of the joined parts. The second part of the cylinder is advantageously color coded to identify the type or needle being carried.

18 Claims, 2 Drawing Sheets

FIG. 4
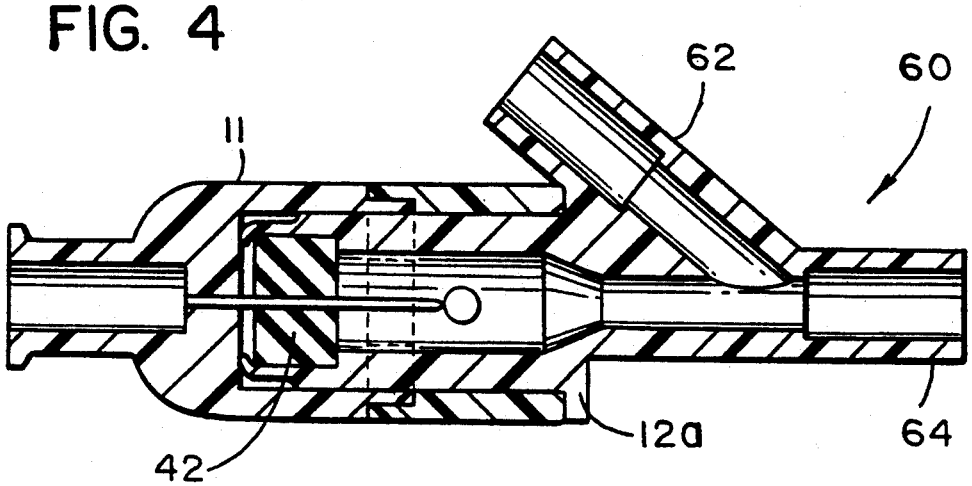
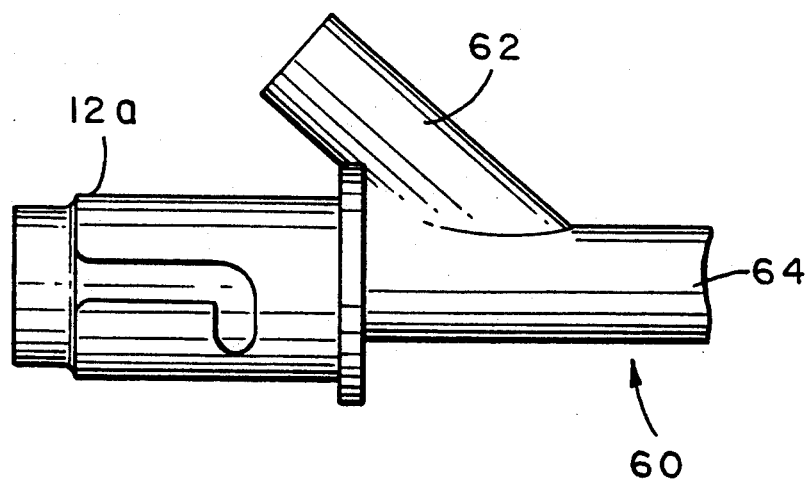
FIG. 5
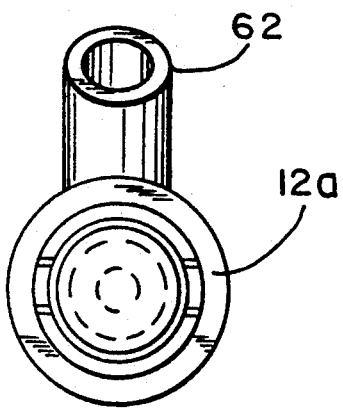
FIG. 5a

# THREE PIECE INTRAVENOUS LINE CONNECTOR

BACKGROUND OF THE INVENTION

1. Field of the Invention

This invention relates to connectors for use with intravenous administration lines and systems in the medical field. The invention more particularly relates to an IV quick-connect/disconnect safety assembly that makes it more convenient to attach and detach a patient to and from an IV system.

2. State of the Art

Intravenous therapy has a long history of use in supplying patients with medicament, nourishment or fluids. One of the problems associated with intravenous therapy of ambulatory patients is that the patient cannot be easily disconnected from and reconnected to an intravenous administration line for short periods of time. To safely and easily disconnect the patient for even a short period of time requires the assistance of skilled medical personnel. The ambulatory patient is often required to be attached to the intravenous system and must wheel a stand holding the IV liquid supply wherever the patient goes. Being restricted in this manner can cause the patient to forgo activities of short duration that would be beneficial to the patient.

It is often necessary for hospital staff to move patients from location to location within the hospital in order to perform tests and certain medical treatments. It is not necessary or desirable to have the patient hooked up to the intravenous system during some of these activities. Removing a patient from an intravenous system and re-establishing the patient on the system takes a substantial amount of time even for a medical professional skilled in the techniques of intravenous therapy. With hospital costs rising dramatically there is considerable advantage in a connector device that allows the medical staff to be able to quickly and safely connect and disconnect a patient from an intravenous therapy administration line while expending a minimum amount of time in doing so.

The prior art has addressed some of the above stated problems. For example, patent 4,511,359 issued to Vaillancourt describes a three-part sterile dialysis connection device for home use. The three parts are a male connector which terminates in a catheter tube; a female connector with a hollow needle secured in place and terminating in a flexible tubing; and a molded septum assembly. Vaillancourt places the molded septum assembly in the receiver end of the female connector. The female connector is assembly into place between the male and female connectors, and into friction fit with the male connector, and also causing the sharpened needle in the female connector to pierce the molded septum assembly. The hollow needle provides a path for fluid flow between the two connector parts. When the male and female connectors are separated, the needle is removed from the self-sealing septum, and the septum assembly remains with and covering the male connector because of its friction fit therewith.

Another three-part home dialysis connection device is described in U.S. Pat. No. 4,810,241 issued to Rogers which provides a sterile connection by mechanical and chemical means. The three parts include two connectors, one attached to an influent tube and the other to the catheter tube, and a cylindrical shaped tube in which there is highly absorbent material saturated with antiseptic. The two connectors in turn connect one to each end of the cylinder. As the end connectors are introduced into the central cylinder connector, they are sterilized by the antiseptic in the cylinder and remain in antiseptic contact during the entire time they are being used for dialysis. A sterile environment is maintained on the catheter tubing side of the IV system only for so long as the catheter side tubing is in the connector cylinder. Care must be taken not to let the disinfectant in the cylinder dry out or evaporate.

A somewhat different solution to the problem was taken by U.S. Pat. No. 4,559,043 issued to Whitehouse, et al. which provides a four-piece assembly including a distal connector, a proximate connector, a septum fitting between and held in place by the distal and proximate connectors, and an adapter with a through bore able to accept a hollow needle, the adapter being used in conjunction with the proximate connector. A hollow needle attached to a standard luer extension T which connects to the adapter is pushed through the adapter needle bore and pierces the septum which is held between the proximate and distal connectors, thereby establishing fluid flow. When the hollow needle attached to the luer T is removed, the septum is sealed, but the needle is exposed, presenting a needlestick hazard.

While these devices of the prior art may be effective for their particular purposes, the requirement for a simple, low-cost, quick-connect/disconnect safety assembly is not filled. The prior art does not show a device which has all of the virtues in a single device of being simple and inexpensive to manufacture, providing standard means such as luer fittings for attachment to other devices, and providing means for shielding the needle after use to prevent accidental needlesticks.

My prior U.S. Pat. No. 5,139,483 (the complete disclosure of which is incorporated herein by reference) teaches an IV quick-connect/disconnect device having molded single piece male and female connectors. The male connector has a male luer-lock on one end, a pair of outwardly extending bayonet knobs on a middle portion and a reduced diameter second end which terminates in a resilient septum. The female connector has a female luer-lock on one end and a receiving cylinder with a pair bayonet cut outs on the other; the luer-lock and the cylinder being separated by a wall through which a hollow needle extends that has been insert molded in the wall. The male and female connectors are mated by sliding the reduced diameter second end of the male connector into the receiving cylinder of the female connector, with the bayonet cutouts of the female connector serving as a track for the extended knobs of the male connector. The connectors are locked into place by bringing the male connector as far forward as possible, and then rotating the male connector such that extending knobs move past a restriction in the cutout and click (lock) into place.

This arrangement overcomes many of the disadvantages of the prior art, but it still has its drawbacks. The female connector is fragile due to the bayonet cut outs and these cut outs form a ragged end surface of the female connector when the connectors are uncoupled. The cut outs can actually catch or snag surgical gloves or other medical equipment. Similarly, the bayonet knobs of the male connector present a ragged surface of the male connector when it is uncoupled from the female connector. Moreover, the bayonet knobs on the male connector sometimes extend slightly beyond the outer surface of the female connecter when the connectors are coupled. The extended bayonet knobs of the male connector result in a less than totally smooth surface and this surface can catch, snag and cause tears in surgical gloves, etc. Unfortunately, there is no easy way to avoid this problem in a two piece assembly because molding requirements dictate the bayonet cut outs be located on the female connector and that the knobs which fit into the cut outs be located on the male connector. Indeed, manufacturing considerations have limited the features of these connectors in several ways and the provided features have dictated some inconvenient manufacturing steps. For example, the resilient septum at the second end of the male connector covers a portion of both the inside and the outside wall surface of the second end and is held in place by a thin plastic shrink band. This is not an ideal configuration since the septum and the shrink band are exposed to wear and can be torn. Additionally, the female connectors may carry either an eighteen or twenty gauge needle depending on the type of fluid to be delivered through the connectors, but there is no simple way of distinguishing the larger gauge needles from the smaller gauge needles without direct comparison.

SUMMARY OF THE INVENTION

It is therefore as the object of the invention to provide a simple, low cost, IV quick-connect/disconnect safety assembly.

Another object is to provide an IV quick-connect/disconnect assembly that is streamlined and has no projections or protruding parts which might catch or snag.

A further object of the invention is to provide an IV quick-connect/disconnect assembly designed so that the needle piercing the septum of the male connector is contained in a shielded area at all times, thereby substantially eliminating the possibility of accidental needlesticks.

Another object of the invention is to provide an IV quick-connect/disconnect assembly that will reduce the average time it takes medical personnel to establish the IV therapy system servicing a patient.

Yet another object of the invention is to provide an IV quick-connect/disconnect assembly that has means at both ends that permit attachment to any type of standard administration lines, extension sets, winged needles, catheters, or other IV medical devices using standard medical attachment means such as luer-locks or luer-slip fittings.

It is still another object of the invention to provide a simple and rapid means for indicating the gauge of the needle carried by the female connector.

An even further object of the invention is to provide an improved construction of the male connector so that the septum is easily attached to the male connector and is protected from tearing, edge wear, and detachment.

It is yet another object of the invention to provide a safety IV Y-injection port having an integral male connector.

In accordance with the objects stated above an IV quick-connect/disconnect assembly is provided and generally comprises a suitably molded single piece male connector and a two piece female connector. The male connector has a male luer-lock on one end, one or more inwardly extending bayonet recesses on the surface of a middle section of reduced diameter, and a second end of further reduced diameter which has a cold rolled edge which encloses a resilient molded septum or the like. The first piece of the female connector has a female luer-lock on one end and a first portion of a receiving cylinder on the other. The luer-lock and the first portion of the cylinder are separated by a wall, and a hollow needle which has been insert molded or bonded in the wall extends therethrough. The second piece of the female connector is the second portion of the receiving cylinder which is preferably sonically welded (or chemical welded or solvent bonded) to the first piece. The second piece has one or more inwardly extending knobs on its inner surface which are arranged to engage the inwardly extending bayonet recesses of the male connector when the reduced diameter second end of the male connector is placed in the receiving cylinder of the female connector. The pointed end of the hollow needle is located in the second portion of the receiving cylinder. The outside cylindrical surfaces of both the male and female connectors (both before and after mating) are smooth with no projections that can catch or snag other medical equipment.

In using the male and female connectors, an IV administration line with a male luer-lock or luer-slip is inserted into the female luer side of the female connector, while an IV winged needle or catheter device that is connected directly to an extension line or the like which terminates in a female luer-lock or luer-slip is connected with the male luer-lock or luer-slip of the male connector. The male and female connectors are mated by sliding the reduced diameter second end of the male connector into the receiving cylinder of the female connector, with the recesses of the male connector serving as a track for the inwardly extending knobs of the receiving cylinder of the female connector. As the male connector is slid forward, the needle in the female connector pierces the resilient septum which permits the flow of liquid through the septum via the hollow needle. The connectors are locked into place by bringing the male connector as far into the female connector as possible, and then rotating the male and/or female connector such that the knobs on the female connector move past restrictions in the recesses in the male connector and both connectors click (lock) into place. Quick release is obtained by rotating the male and/or female connector in the opposite direction and pulling the male connector straight out relative to the female connector. When the male and female connectors are separated, the needle in the female connector is withdrawn from the self-sealing resilient septum held in the reduced diameter second end of the male connector.

The male connector of the IV quick-connect/disconnect safety assembly may be fabricated as the termination of a branch of a Y-injection port. This makes it possible to add a second source of IV fluid via a bag, bottle, or syringe.

Preferred aspects of the invention include: color coding the second piece of the female connector to indicate the gauge of the needle carried by the female connector; providing the coupling surfaces of the first and second pieces of the female connector with facets to prevent rotation of the pieces; constructing the first piece of the female connector of clear plastic so that the connection can be checked for leaks; providing the male and female connectors with finger gripping surfaces to facilitate the twisting connection of the connectors.

Additional objects and advantages of the invention will become apparent to those skilled in the art upon

BRIEF DESCRIPTION OF THE DRAWINGS

FIG. 2b is a cross section along line B—B of FIG. 2a.

FIG. 4 is a longitudinal cross section of a Y-injection port with integrated male connector according to the invention shown with an attached female connector.

FIG. 5 is a side elevation view of the Y-injection port of FIG. 4 with the female connector removed.

FIG. 5a is an end view of the second end of the Y-injection port of FIG. 5.

DETAILED DESCRIPTION OF THE INVENTION

Figure 1:
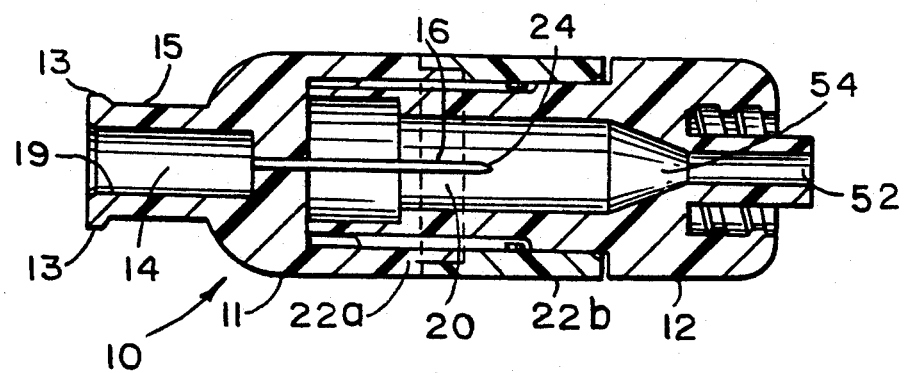
FIG. 1 is a longitudinal cross section through the IV quick-connect/disconnect safety assembly invention.
Figure 1A:
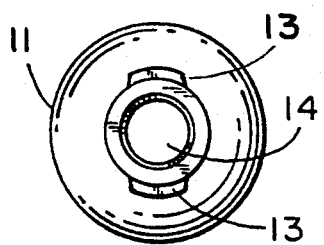
FIG. 1a is an end view of the first end of the female connector.
Figure 1B:
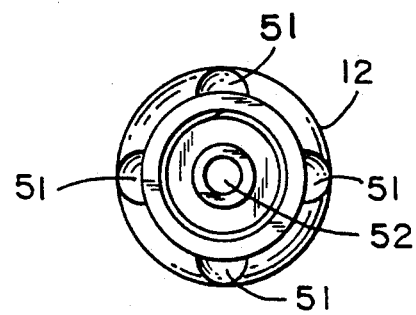
FIG. 1b is an end view of the first end of the male connector.
Figure 2:
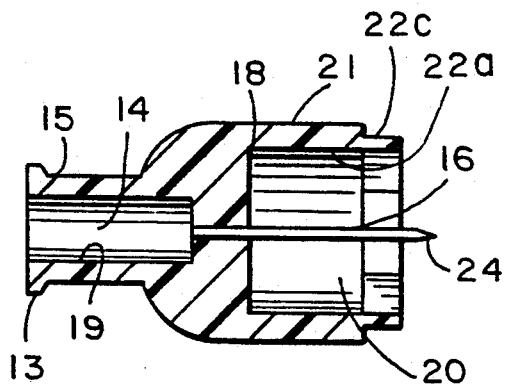
FIG. 2 is a longitudinal cross section through the first portion of the female connector.

As seen in FIGS. 1, 1a, 1b, 2, 2a, 2b, and 2c, the IV quick-connect/disconnect safety assembly 10 of the invention comprises a female connector 11 and male connector 12. The female connector 11, as shown in FIG. 2, has a reduced end 15 and an enlarged end 21 separated by a dividing wall 18. The reduced end 15 forms a female luer lock with a female luer 19 and a lip or tab 13. The enlarged end 21 is defined by a cylinder wall 22a which surrounds a first portion of a cylindrical receiving area 20. The receiving cylinder wall 22a has an outer faceted surface 22c for coupling with a cylinder extension 22b. The cylinder extension 22b has an inner faceted surface 22d which is preferably coupled by sonic welding to the outer faceted surface 22c of cylinder wall 22a and surroundingly defines a second portion of the receiving area 20. Instead of sonic welding, it will be appreciated that solvent bonding or chemical welding may be utilized.

A hollow needle 16 is bonded or preferably insert molded in the dividing wall 18 so that the pointed end 24 of the needle 16 is located in the receiving area 20. The hollow needle forms a passageway between the tapered bore 14 of the female luer lock and the receiving area. The female connector is molded from preferably clear plastic or other acceptable materials. Clear plastic is preferred so that the connector can be inspected for leaks.

Figure 2A:
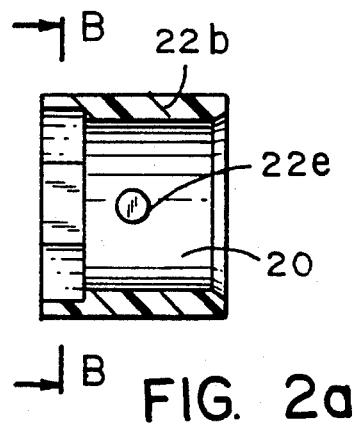
FIG. 2a is a longitudinal cross section through the second portion of the female connector.
Figure 2B:
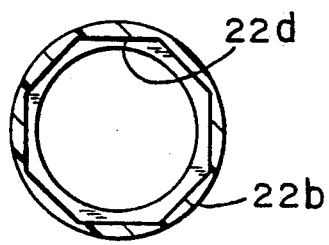
Figure 2C:
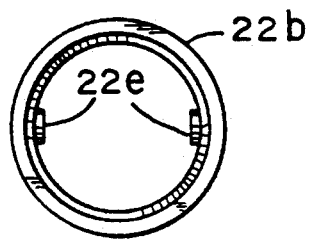
FIG. 2c is an end view of the second end of the female connector.

The cylinder extension 22b shown in FIGS. 2a-2c is preferably a molded piece having one or more preferably rounded knobs 22e extending radially inward. The cylinder extension 22b is preferably color coded to indicate the gauge of the needle carried in the female connector 11.

Figure 3:
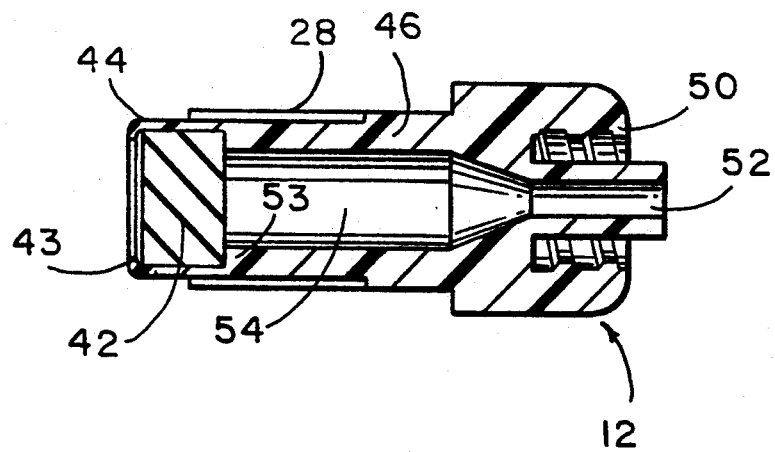
FIG. 3 is a longitudinal cross section through the male connector of the IV quick-connect/disconnect safety assembly invention.
Figure 3A:
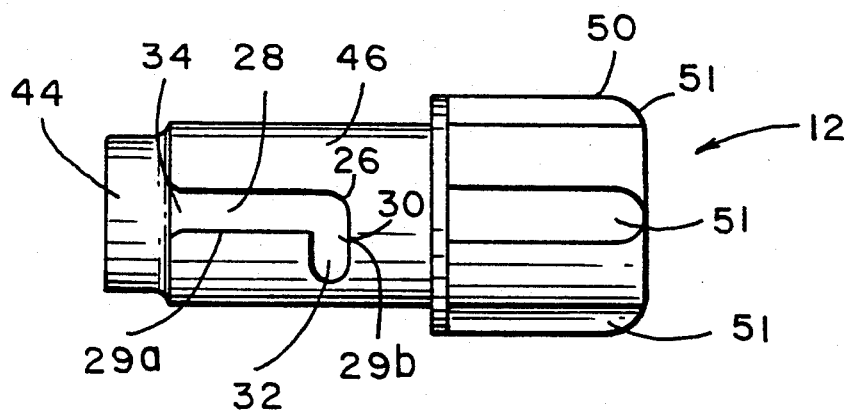
FIG. 3a is a top view of the male connector.
Figure 3B:
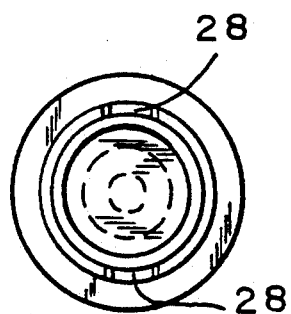
FIG. 3b is an end view of the second end of the male connector.

The male connector 12, shown in FIGS. 3, 3a, and 3b, has a a first end 50, a middle portion 46, and a second end 44. The first end 50 is essentially a male luer lock 52 with external rounded ribs 51 which form a finger grip. The middle portion 46 of the male connector 12 is of reduced outer diameter relative to the first end 50 and has one or more bayonet type recesses 28. Recesses 28, as seen in FIG. 3, do not extend through the plastic middle portion 46, but provide a track with a bottom surface. The recesses have a first section 29a which is parallel to the long axis of the male connector and a second section 29b which is perpendicular to and a continuation of the first section in the perpendicular direction. The second section 29b terminates in a circular area 32 which is partially defined by a restriction 30 which reduces the entry way into a circular area 32. Entrance 34 to the recess 28 is at the end of the middle portion, and is slightly flared in order to help the knobs 22e of the female extender 22b to enter the recess 28.

Male connector 12 terminates in a second end 44 of further reduced outer diameter. The second end 44 holds a resilient septum 42 fitted in and covered by a cold rolled edge 43 of the exterior wall surface of second end 44. The first end 50, the middle portion 46, and the second end 44 of the male connector 12 encompass a bore 54 which preferably enlarges as it proceeds from the first end 50 towards the second end 44 of the male connector 12. It will be appreciated that the bore 54 is preferably stepped behind the septum such that the cold rolled edge 43 of end 44 and step 53 of the bore 54 form a secure housing for the septum 42.

In using the male and female connectors of the invention as shown in FIG. 1, the male connector is positioned so that the reduced diameter second end 44 of the male connector is introduced into the receiving chamber 20 of the female connector 11 with the rounded knobs 22e of the female connector being in position at the openings 34 of the bayonet recesses 28 in the male connector. The male connector is pushed forward as far as it will go until the knobs come in contact with the turn 26 in recesses 28. The male connector is then rotated so that the knobs go past the restriction 30 in the radius wall and come to rest in the recess pockets 32. The recess pockets 32 in conjunction with the restriction 30 apply sufficient force to the knobs to securely hold the assembly together. When the male and female connectors are locked together, a distinct audible click is typically heard and signals the person practitioner that the connection is secure. In addition, the outer surfaces of the connectors form a substantially smooth surface.

When the reduced diameter end 44 of the male connector 12 is pushed forward as described above, the needle 16 of the female connector 11 pierces the septum 42 and permits fluid to flow from chamber 14 through the needle 16 and into bore 54.

When the male and female connectors are to be disconnected, the male connector 12 is rotated so that the knobs 22e in the female connector 11 move past the restriction 30 in the bayonet recess in middle portion of the male connector 12. Then the male connector 12 is pulled straight back so that the knobs of the female connector pass down the longitudinal part of the recesses to the entry way 34. As the male connector is removed, the needle is withdrawn from the resilient self-sealing septum 42 which immediately seals and cuts off fluid flow. The self- sealing septum 42 also keeps out bacteria, dirt, dust and other contaminates from the patient side of the IV administration system. When disconnected, the needle 16 in the female connector 11 is shielded by the receiving cylinder wall 22a and the extension cylinder 22b so that inadvertent needlesticks are reduced to a minimum. This is an important safety feature.

In the preferred embodiment, the middle portion 46 of the male connector 12 is sized to loosely contact the receiving cylinder walls 22a, 22b of the female connector when mating, thereby serving the added function of centering the male connector so that the needle point 24 is centered when it pierces the septum 42. The line connector device may be reused without negative effect on the functioning of the device.

Turning now to FIGS. 4, 5, and 5a, a Y-injection port 60 incorporating the male connector 12a of the invention is shown. The Y-injection port is typically used by connecting IV tubing to portions 62 and 64. The male connector 12a of the Y-injection port allows other medicaments and fluids to be administered through the septum fitted male connection shown as the termination of the branch of the Y-injection port, such as by utilizing the female connector 11 of the invention.

There have been described and illustrated herein a quick-connect/disconnect device for an IV administration line system. While particular embodiments of the invention have been described, it is not intended that the invention be limited thereby, as it is intended that the invention be as broad in scope as the art will allow. Thus, it will be appreciated by those skilled in the art that the term "IV fluid" is intended to be understood in a broad sense to include nutrients, blood, blood products, or other medical fluids, and the term "administration" is used in its broad sense to include the dispensing or collection of the IV fluid. Further, while the female connector was illustrated as preferably having a female luer-lock on one end, and the male connector was illustrated as preferably having a male luer-lock on one end, it will be appreciated that, although not preferred, simple luer slips could be utilized in lieu of luer locks. Also, while the central bore in the male connector was described as increasing in size as it extended from the male luer lock end to the septum end, it will be appreciated that the central bore could be of substantially constant diameter, or of changing diameters which do not increase in size as described. Further yet, it should be appreciated that while the female connector was described as having a hollow needle insert molded or bonded into a wall dividing the first piece of the female connector, the needle could be or formed in different manners. For example, the needle could be a plastic needle or piercing device formed as part of the molding process as an integral part of the first piece of the female connector. In addition, while the male connecter is shown and described as having finger gripping ribs, ribs may be provided on the female connector as well or in lieu of the ribs on the male connector. Therefore, it will be appreciated by those skilled in the art that yet other modifications could be made to the provided invention without deviating from its spirit and scope as so claimed.

I claim:

1. A three piece fluid line connection assembly for permitting the coupling and uncoupling of an influent supply line terminating in a first male luer and an effluent supply line starting with a first female luer, the assembly comprising:

a) a two piece female connector, a first one of said two pieces having first and second hollow portions, a dividing wall separating said first and second hollow portions, and a hollow needle having a first sharp end, said first hollow portion having a first substantially cylindrical wall forming a first part of a receiving chamber with a first substantially open end having a first stepped diameter, said second hollow portion having a second substantially cylindrical wall with an inside surface forming a second female luer for mating with said first male luer of said influent supply line, and an outside surface of reduced outer diameter relative to the outer diameter of most of said first substantially cylindrical wall, said hollow needle forming a passageway through said dividing wall and connecting said receiving chamber and said second female luer, with said first sharp end of said hollow needle extending into said receiving chamber, a second one of said two pieces having a second substantially cylindrical wall forming a second part of said receiving chamber and having a second substantially open end with a second stepped diameter which couples with said first substantially open end, and a third substantially open end, and said second substantially cylindrical wall having at least one inwardly extending knob; and b) a male connector with a hollow first end cylindrical portion having a first opening, a hollow middle body cylindrical portion, a hollow second end cylindrical portion with a second male luer for mating with said first female luer of said effluent supply line extending therefrom, and a resilient septum, said hollow first end cylindrical portion containing said resilient septum in said first opening, and said hollow first end cylindrical portion and said hollow middle body cylindrical portion being of reduced outer diameters relative to the inner diameter of said receiving chamber of said female connector, and said hollow middle body cylindrical portion having at least one inwardly extending bayonet recess, wherein said bayonet recess includes a locking section, and said bayonet recess and said inwardly extending knob are dimensioned such that said inwardly extending knob is received in said bayonet recess and can lock in said locking section, and the axial distance between said inwardly extending knob and the sharp end of said needle along a longitudinal axis of said female connector is smaller than the axial distance between said septum and the locking section of said bayonet recess along a longitudinal axis of said male connector such that when said said female connector and male connector are mated, said sharp end of said needle pierces said septum, wherein said two piece female connector and said male connector have outer surfaces which present a substantially smooth continuous surface when said two piece female connector and said male connector are mated.

2. A fluid line connection assembly according to claim 1, wherein:

said third substantially open end of said second of said two pieces extends beyond said sharp end of said needle so as to reduce needlestick injuries.

3. A fluid line connection assembly according to claim 2, wherein:
said dividing wall of said female connector has a smooth outer surface which tapers from the outer diameter of said receiving chamber to the outer diameter of said second hollow portion of said female connector.

4. A fluid line connection assembly according to claim 3, wherein:
said second female luer of said female connector comprises a female luer-lock.

5. A fluid line connection assembly according to claim 3, wherein:
said second male luer of said male connector comprises a male luer-lock.

6. A fluid line connection assembly according to claim 4, wherein:
said second male luer of said male connector comprises a male luer-lock.

7. A fluid line connection assembly according to claim 1, wherein:
said second female luer of said female connector comprises a female luer-lock, and
said second male luer of said male connector comprises a male luer-lock.

8. A fluid line connection assembly according to claim 1, wherein:
said first opening of said male connector is tapered in order to retain said resilient septum.

9. A fluid line connection assembly according to claim 6, wherein:
said first opening of said male connector is tapered in order to retain said resilient septum.

10. A fluid line connection assembly according to claim 8, wherein:
said resilient septum is a self-sealing resilient septum.

11. A fluid line connection assembly according to claim 1, wherein:
said male connector and female connector are molded from plastic.

12. A fluid line connection assembly according to claim 1, wherein:
said male connector and said female connector are molded from plastic, and
said hollow second end cylindrical portion of said male connector is molded with indentations in its outer surface as finger grip means for said male connector.

13. A fluid line connector assembly according to claim 6, wherein:
said male connector and said female connector are molded from plastic, and
said hollow second end cylindrical portion of said male connector is molded with indentations in its outer surface as finger grip means for said male connector.

14. A fluid line connector assembly according to claim 1, wherein:
said first substantially open end has a reduced outer diameter, and
said second substantially open end has a reduced inner diameter such that said second substantially open end fits snugly over said first substantially open end.

15. A fluid line connector assembly according to claim 1, wherein:
said first substantially open end has a faceted surface, and
said second substantially open end has a faceted surface such that when said first and second substantially open ends are coupled relative rotation of said first and second pieces is prevented.

16. A fluid line connector assembly according to claim 1, wherein:
said second piece is color coded to indicate a type of needle carried in said female connector.

17. A fluid line connector assembly according to claim 1, wherein:
said first and second substantially open ends are coupled by one of sonic welding and solvent bonding.

18. A fluid line connector assembly according to claim 11, wherein:
said bayonet recess in said male connector extends only partially into a plastic wall of said male connector.

* * * * *